United States Patent
Babu et al.

(10) Patent No.: US 9,558,515 B2
(45) Date of Patent: Jan. 31, 2017

(54) RECOMMENDING FOOD ITEMS BASED ON PERSONAL INFORMATION AND NUTRITIONAL CONTENT

(71) Applicant: Wal-Mart Stores, Inc., Bentonville, AR (US)

(72) Inventors: Narendra Babu, Cupertino, CA (US); Ramesh Kozhissery, Bangalore (IN); Rijul Jain, New Delhi (IN)

(73) Assignee: WAL-MART STORES, INC., Bentonville, AR (US)

(*) Notice: Subject to any disclaimer, the term of this patent is extended or adjusted under 35 U.S.C. 154(b) by 0 days.

(21) Appl. No.: 14/548,204

(22) Filed: Nov. 19, 2014

(65) Prior Publication Data

US 2016/0140644 A1    May 19, 2016

(51) Int. Cl.
  G06F 17/00    (2006.01)
  G06Q 30/06    (2012.01)

(52) U.S. Cl.
  CPC ...... *G06Q 30/0631* (2013.01); *G06Q 30/0633* (2013.01)

(58) Field of Classification Search
  CPC .................. G06Q 30/0631; G06Q 30/0633
  USPC ................................................ 235/375, 383
  See application file for complete search history.

(56) References Cited

U.S. PATENT DOCUMENTS

| | | | |
|---|---|---|---|
| 7,680,690 B1* | 3/2010 | Catalano | G06Q 30/02 186/38 |
| 7,835,946 B2* | 11/2010 | Goren | G06Q 30/02 705/26.7 |
| 8,684,922 B2* | 4/2014 | Tran | A61B 5/6816 600/300 |
| 2008/0189172 A1* | 8/2008 | Goren | G06Q 30/02 705/14.23 |
| 2009/0055199 A1* | 2/2009 | Yusuf | G06Q 50/12 705/15 |
| 2011/0184247 A1* | 7/2011 | Contant | G06Q 10/10 600/300 |
| 2011/0318717 A1* | 12/2011 | Adamowicz | G09B 19/0092 434/127 |
| 2012/0233002 A1* | 9/2012 | Abujbara | G06Q 10/06 705/15 |
| 2013/0085345 A1* | 4/2013 | Geisner | G06Q 30/00 600/300 |
| 2013/0095459 A1* | 4/2013 | Tran | A61B 5/6816 434/247 |
| 2013/0196297 A1* | 8/2013 | Anwar | G06F 19/3475 434/236 |

(Continued)

Primary Examiner — Paultep Savusdiphol
(74) Attorney, Agent, or Firm — Bryan Cave LLP

(57) ABSTRACT

The present invention extends to systems, methods, and computer program products for recommending food items based on personal information and nutritional content. A registered customer has members in a customer group. The registered customer provides nutritional information for members of the group (e.g., family members) to a merchant computer system. The merchant computer system uses the nutritional information to recommend food items to the customer. As a customer shops, the merchant computer system compares the nutritional content of the shopping cart items with nutritional needs of the customer. Recommendations are furnished to the customer based on the shopping cart content and the nutritional needs of the customer.

22 Claims, 4 Drawing Sheets

(56) References Cited

U.S. PATENT DOCUMENTS

| | | | |
|---|---|---|---|
| 2014/0214446 A1* | 7/2014 | Nusbaum | G09B 19/00 705/2 |
| 2014/0220516 A1* | 8/2014 | Marshall | G09B 19/0092 434/127 |
| 2014/0236622 A1* | 8/2014 | Southam | G06Q 30/02 705/2 |
| 2015/0025991 A1* | 1/2015 | Shaw | G06Q 50/01 705/26.2 |
| 2015/0206450 A1* | 7/2015 | Wayman | G09B 5/02 434/127 |

* cited by examiner

RECOMMENDING FOOD ITEMS BASED ON PERSONAL INFORMATION AND NUTRITIONAL CONTENT

CROSS-REFERENCE TO RELATED APPLICATIONS

Not applicable.

BACKGROUND

1. Field of the Invention

This invention relates generally to the field of nutrition management. More specifically, the invention relates to recommending food items to meet nutritional needs of a customer based on a nutritional profile for the customer and food item nutritional information.

2. Related Art

When a customer shops online or at a store for groceries, that customer may desire to purchase food items that meet their nutritional needs or the nutritional needs of their family. A food item's package generally has a nutritional table printed on the package. For a non-packaged food item, such as a produce item, it is possible to get nutritional information from an online source such as a government agency, a consumer group, a store or other entity. Thus, nutritional information for individual items is generally easy to retrieve and can be stored on computers, cell phones, tablets and other such devices.

Even more to customer useful is aggregated information that combines the nutritional information for multiple food items. Aggregated information can be used to help a customer meet their overall nutritional requirements. However, the time and effort required to aggregate nutritional information from different food items can be relatively time consuming. As such, many customers lack the time and/or desire to invest in aggregating nutritional information for multiple food items. However, without aggregated nutritional information, it can be challenging for a customer to determine what food items to purchase to meet their nutritional requirements.

In some cases, different family members may also have different nutritional needs based on age, height, weight, food preferences, and medical problems. As such, aggregating nutritional information to satisfy nutritional needs of a family can be even more burdensome. For some customers, cost is also a factor. Thus, in general, it is challenging for a customer to purchase food items that meet the nutritional needs of their family and do so while considering all the factors that influence that purchase.

BRIEF DESCRIPTION OF THE DRAWINGS

The specific features, aspects and advantages of the present invention will become better understood with regard to the following description and accompanying drawings where.

DETAILED DESCRIPTION

Figure 1:
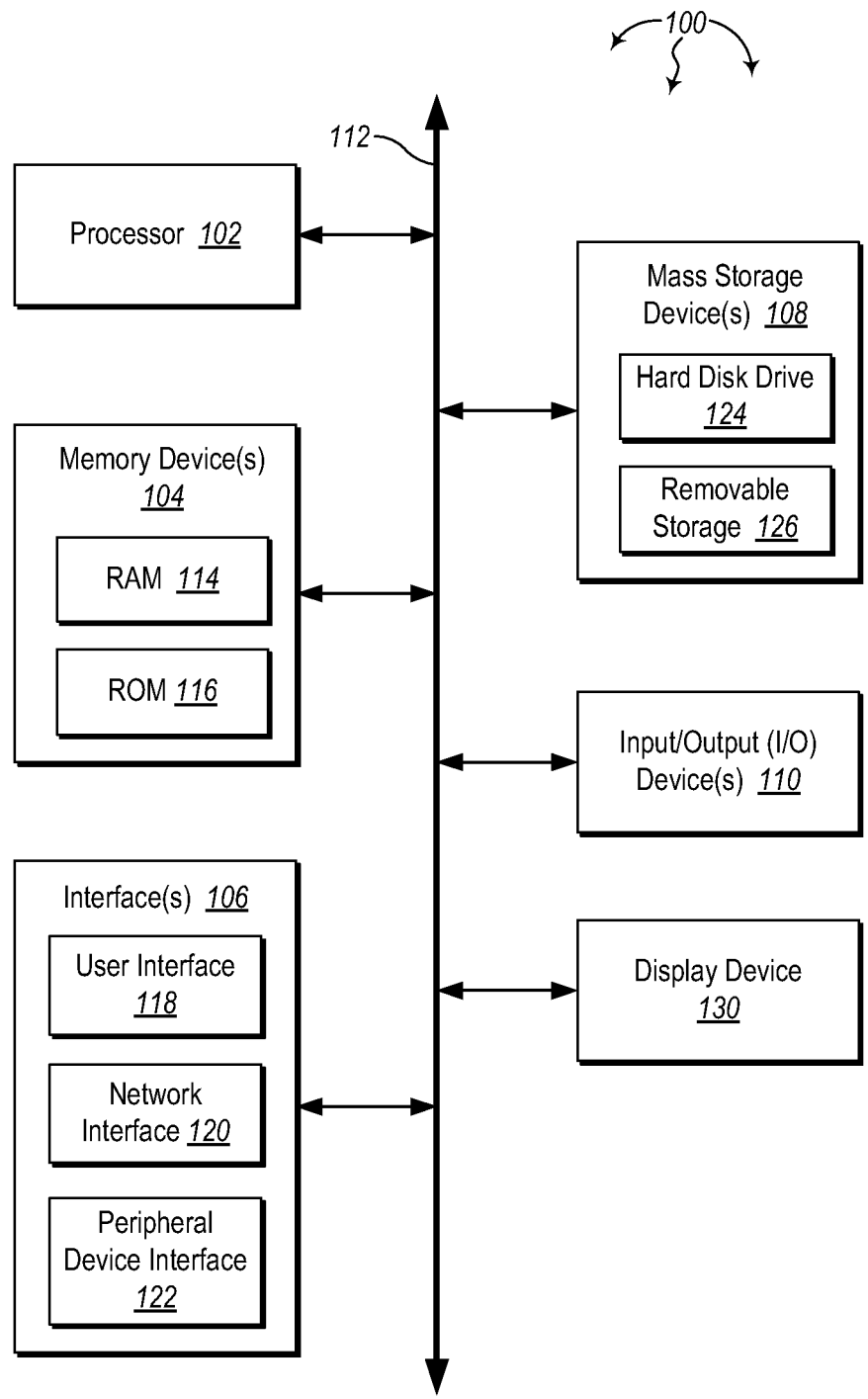
FIG. 1 illustrates an example block diagram of a computing device.

The present invention extends to systems, methods, and computer program products for recommending food items based on personal information and nutritional content.

In the following description of the present invention, reference is made to the accompanying drawings, which form a part hereof, and in which is shown by way of illustration specific embodiments in which the invention is may be practiced. It is understood that other embodiments may be utilized and structural changes may be made without departing from the scope of the present invention.

Embodiments of the present invention may comprise or utilize a special purpose or general-purpose computer including computer hardware, such as, for example, one or more processors and system memory, as discussed in greater detail below. Embodiments within the scope of the present invention also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, embodiments of the invention can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. RAM can also include solid state drives (SSDs or PCIx based real time memory tiered Storage, such as FusionIO). Thus, it should be understood that computer storage media (devices) can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, various storage devices, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Embodiments of the invention can also be implemented in cloud computing environments. In this description and the following claims, "cloud computing" is defined as a model for enabling ubiquitous, convenient, on-demand network access to a shared pool of configurable computing resources (e.g., networks, servers, storage, applications, and services) that can be rapidly provisioned via virtualization and released with minimal management effort or service provider interaction, and then scaled accordingly. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

It is further noted that, where feasible, functions described herein can be performed in one or more of: hardware, software, firmware, digital components, or analog components. For example, one or more application specific integrated circuits ("ASICs") can be programmed to carry out one or more of the systems and procedures described herein. Certain terms are used throughout the following description and Claims to refer to particular system components. As one skilled in the art will appreciate, components may be referred to by different names. This document does not intend to distinguish between components that differ in name, but not function.

In general, a mobile device can receive user input from a registered customer of a merchant. The user input selects one or more food items for placement in a shopping cart of the merchant. The registered customer includes a group of one or more (e.g., family) members and has a customer nutritional profile available to the retailer. The customer nutritional profile can be derived from characteristics associated with the registered customer, including customer characteristics applicable to the group of one or more members and member characteristics applicable to individual members. The selection of one or more food items is forwarded to a merchant computer system.

The merchant computer system accesses the selection of one or more food items for the registered customer. The merchant computer system accesses the customer nutritional profile. The merchant computer system calculates a cumulative nutritional content of the one or more food items from item nutritional profiles for each of the one or more food items. The merchant computer system compares the customer nutritional profile to the cumulative nutritional content to determine that purchase of the one or more food items fails to satisfy a nutritional requirement of the registered customer.

The merchant computer system identifies an additional food item that satisfies the nutritional requirement based on the customer nutritional profile and the nutritional content of the additional food item. The merchant computer system sends the recommended additional food item to the mobile device. The mobile device receives the recommended additional food item from the computer system.

FIG. 1 illustrates an example block diagram of a computing device 100. Computing device 100 can be used to perform various procedures, such as those discussed herein. Computing device 100 can function as a server, a client, or any other computing entity. Computing device 100 can perform various communication and data transfer functions as described herein and can execute one or more application programs, such as the application programs described herein. Computing device 100 can be any of a wide variety of computing devices, such as a mobile telephone or other mobile device, a desktop computer, a notebook computer, a server computer, a handheld computer, tablet computer and the like.

Computing device 100 (e.g., a general purpose computer, special purpose computer, or special purpose processing device) includes one or more processor(s) 102, one or more memory device(s) 104, one or more interface(s) 106, one or more mass storage device(s) 108, one or more Input/Output (I/O) device(s) 110, and a display device 130 all of which are coupled to a bus 112. Processor(s) 102 include one or more processors or controllers that execute instructions stored in memory device(s) 104 and/or mass storage device(s) 108. Processor(s) 102 may also include various types of computer-readable media, such as cache memory.

Memory device(s) 104 include various computer-readable media, such as volatile memory (e.g., random access memory ("RAM") 114) and/or nonvolatile memory (e.g., read-only memory ("ROM") 116). Memory device(s) 104 may also include rewritable ROM, such as Flash memory.

Mass storage device(s) 108 include various computer readable media, such as magnetic tapes, magnetic disks, optical disks, solid state memory (e.g., Flash memory), and so forth. As shown in FIG. 1, a particular mass storage device is a hard disk drive 124. Various drives may also be included in mass storage device(s) 108 to enable reading from and/or writing to the various computer readable media. Mass storage device(s) 108 include removable media 126 and/or non-removable media.

Computer-executable instructions can be stored in memory device(s) 104 and/or mass storage device(s) 108. Computer-executable instructions comprise, for example, instructions and data which, when executed at a processor 102, cause computing device 100 to perform a certain function or group of functions, including those of the invention. The computer executable instructions may be, for example, binaries, intermediate format instructions such as assembly language, or even source code.

I/O device(s) 110 include various devices that allow data and/or other information to be input to or retrieved from computing device 100. Example I/O device(s) 110 include cursor control devices, keyboards, keypads, microphones, monitors or other display devices, speakers, printers, network interface cards, modems, cameras, lenses, CCDs or other image capture devices, and the like.

Display device 130 includes any type of device capable of displaying information to one or more users of computing device 100. Examples of display device 130 include a monitor, display terminal, video projection device, and the like.

Interface(s) 106 include various interfaces that allow computing device 100 to interact with other systems, devices, or computing environments. Example interface(s) 106 can include any number of different network interfaces 120, such as interfaces to personal area networks ("PANs"), local area networks ("LANs"), wide area networks ("WANs"), wireless networks (e.g., near field communication ("NFC"), Bluetooth, Wi-Fi, etc. networks), and the Internet. Other interfaces include user interface 118 and peripheral device interface 122.

Bus 112 allows processor(s) 102, memory device(s) 104, interface(s) 106, mass storage device(s) 108, and I/O device(s) 110 to communicate with one another, as well as other devices or components coupled to bus 112. Bus 112 represents one or more of several types of bus structures, such as a system bus, PCI bus, IEEE 1394 bus, USB bus, and so forth.

Figure 2:
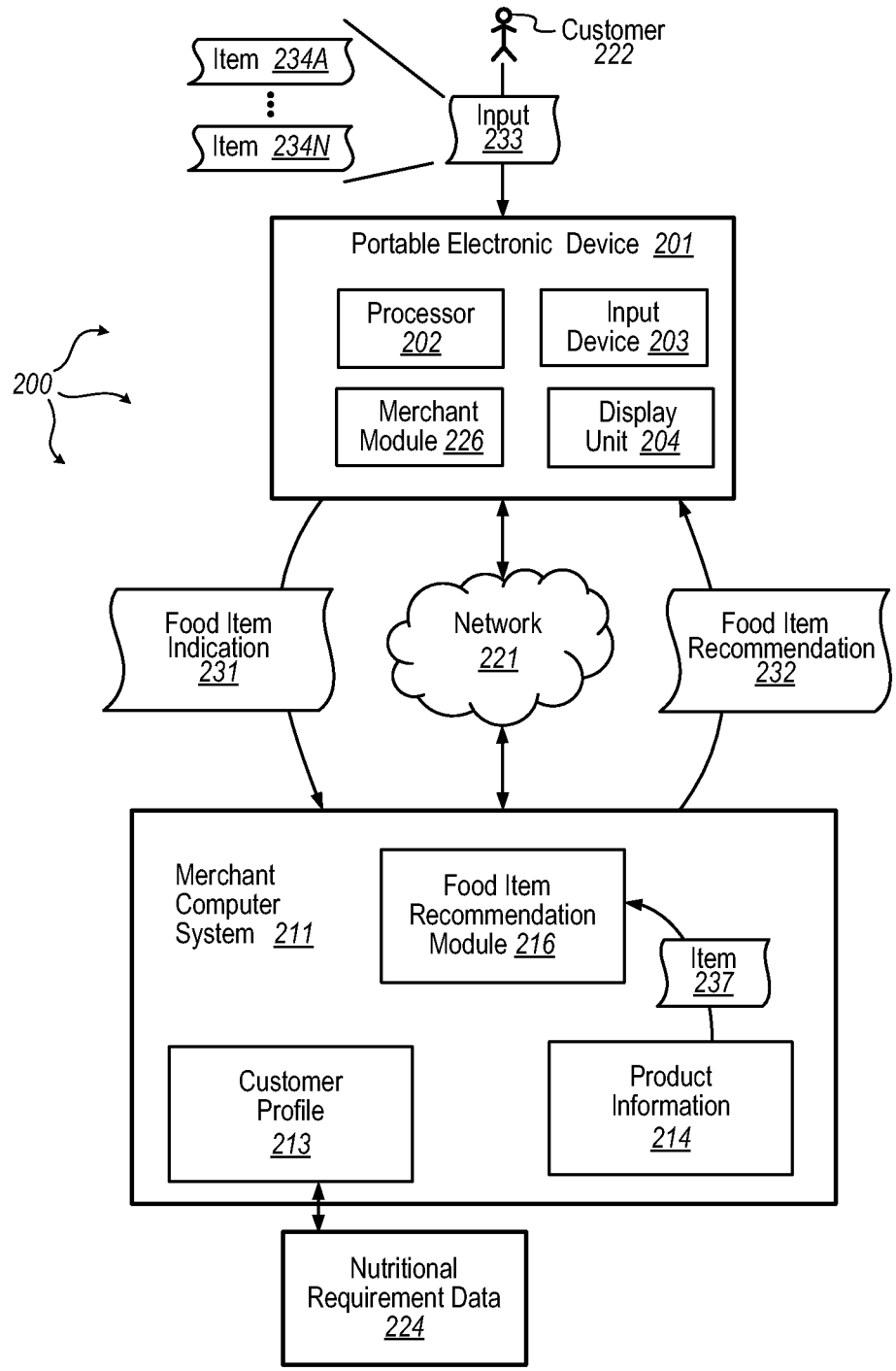
FIG. 2 illustrates an example computer architecture that facilitates recommending food items.

FIG. 2 illustrates an example computer architecture 200 that facilitates recommending food items. As depicted, computer architecture 200 includes portable electronic device 201, merchant computer system 211, and network 221. Network 221 can comprise a local area network (LAN), a wide area network (WAN), or any other type of communication network. In one exemplary embodiment, network 221 comprises the Internet, and messages are communicated across network 220 using transmission control protocol/Internet protocol (TCP/IP). However, other types of networks and other types of protocols can be used.

As depicted, merchant computer system 200 includes customer profile 213 (e.g., including nutritional profiles for one or more members of a customer) and product information 214. Merchant computer system 211 can also include shopping cart functionality or be linked to another computer system (either owned by the merchant or a third party) that includes shopping cart functionality.

Portable electronic device 201 can be belong to (or be used by) customer 222. As depicted, portable electronic device 200 includes processor 202, input device 203, display unit 204, and merchant module 226. Portable electronic device 201 is configured to provide for customer sign-on using the input device 210, such as a keyboard, and to establish a link, via network 221, to merchant computer system 211.

Customer 222 can register (e.g., using merchant module 226) for a nutritional service offered by a merchant. When customer 222 registers, customer 222 can furnishes information that allows the merchant to recommend food items to customer 222 based on provided profile information. For example, customer 222 can provide information about members of a group, such as family members, and can include for each member, a name, date of birth, gender, height, weight, preferred foods, nutritional medical disorders (food allergies, diabetes, other diseases, metabolic disorders, celiacs, etc.), and other information. Entered profile information can be stored in customer profile 213.

Registration for the nutritional service provides the merchant with information (stored in customer profile 213) for making appropriate food item recommendations to customer 222. After customer registration, merchant computer system 211 can begin to track a food purchase history for customer 222. Alternately, merchant computer system 221 can access an existing food purchase history. In one aspect, customer 222 may have previously registered for one or more other merchant programs (e.g., a rewards program) that already track food purchase history. Merchant computer system 211 can access the food purchase history. An access food purchase history can be used to supplement customer profile 213. In general, food item recommendation module 216 can used information contained in customer profile 213 to make food item recommendations for customer 222.

Merchant computer system 211 also stored (or least has access to) nutritional requirement data 224. Nutritional requirement data 224 can include baseline nutritional requirements for individuals based on demographic characteristics. In order to establish the nutritional requirements for each member of a customer 222's group (e.g., a family member), merchant computer system 211 can refer to nutritional requirement data 224. For example, if a member is a 10 year old male, that member characteristic is linked to a child's nutritional profile consistent with a 10 year old male. Nutritional requirement data 224 can be obtained from one or more of a variety of sources, such as, for example the Center for Disease Control, the Food and Drug Administration, the Mayo Clinic, numerous medical schools, and other authoritative sources. Nutritional requirements for individual members of customer 222 can stored in or linked to customer profile 213.

Merchant computer system 211 also includes or has access to product information 214. Product information 214 can include food item information, including nutritional information and prices, for food items offer by a merchant. Nutritional information for food items may be available from several sources. For example, nutritional information is printed on the package of each food item. In addition, nutritional information is retrievable from a supplier of a food item. For packaged food items, nutritional information can be associated with a barcode for a food item. Although a produce item may not have a bar code, a produce item can have an attached unique identifier. Nutritional information for a produce item is available from various sources, such as the Department of Agriculture, The Food and Drug Administration, consumer groups and other groups. As such, product information 214 can include a unique identifier, nutritional information, and price for each food item offered by the merchant. Product information 214 can be updated to account for daily changes in food item prices, introduction of new food items, merchant and producer sale incentives and other factors.

Further, merchant module 226 is configured to notify merchant computer system 211 when a food item is placed in a shopping cart, and upon request from merchant computer system 211, can furnish a unique identity of that food item. Input device 203 can include an identity detector for food items. The identity detector can be bar code reader, RFID detector, other known detector, or future detector available to retail stores. Identifies for unpackaged goods can be entered by detecting or by a user input through a keyboard of input device 203. As such, merchant module 226 can identify food items that customer 222 places in a shopping cart and can indicate those food items to merchant computer system 211.

Generally, as food items in the shopping cart become known to merchant computer system 211, food item recommendation module 216 can calculate a combined nutritional content of the food items. Food item recommendation module 216 can compare the combined nutritional content with nutritional requirements in customer nutritional profile 213. Where items in a shopping cart leave a deficiency in nutritional requirements for one or more members of customer 222, food item recommendation module 216 generates a recommendation for one or more food items to satisfy the deficiency. Food item recommendation module 216 can send the recommendation to portable electronic device 201.

As such, in one aspect, food item recommendation module 216 is configured to identify and recommend food items that help customer 222 meet nutritional requirements.

Figure 3:
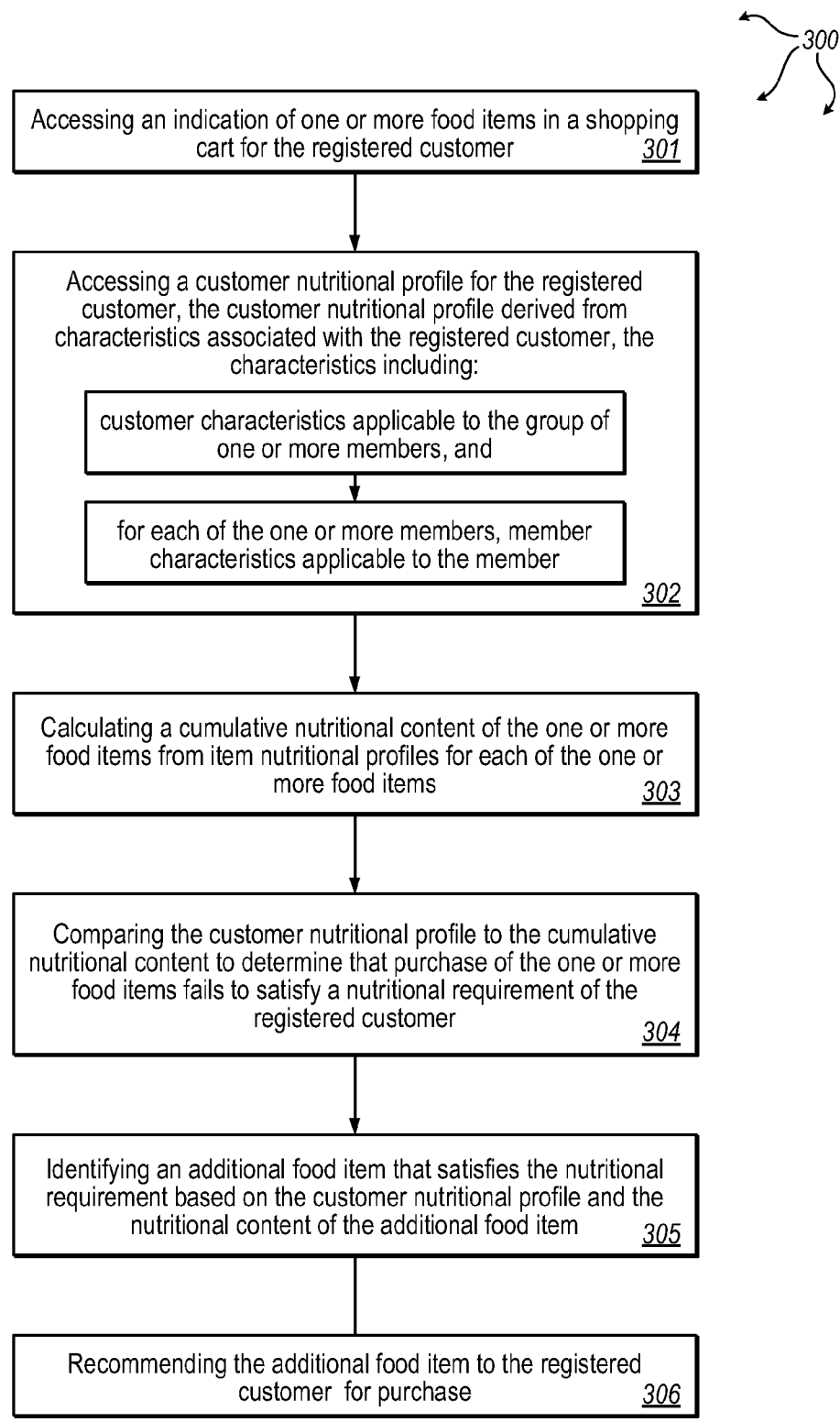
FIG. 3 illustrates a flow chart of an example method for recommending food items.

FIG. 3 illustrates a flow chart of an example method 300 for recommending food items. Method 300 will be described with respect to the components and date in computer architecture 200.

Method 300 includes accessing an indication of one or more food items in a shopping cart for the registered customer (301). For example, food item recommendation module 216 can access food item indication 231 from portable electronic device 201. Food item indication 231 can indicate that customer 222 has selected items 234A-234N for purchase.

Method 300 includes accessing a customer nutritional profile for the registered customer, the customer nutritional profile derived from characteristics associated with the registered customer, the characteristics including customer characteristics applicable to the group of one or more members, and for each of the one or more members, member characteristics applicable to the member (302). For example, food item recommendation module 216 can access customer profile 213 for customer 222.

Method 300 includes calculating a cumulative nutritional content of the one or more food items from item nutritional profiles for each of the one or more food items (303). For example, food item recommendation module 216 can refer to product information 214 to calculate the cumulative nutritional content of food items 234A-234N.

Method 300 includes comparing the customer nutritional profile to the cumulative nutritional content to determine that purchase of the one or more food items fails to satisfy a nutritional requirement of the registered customer (304). For example, food item recommendation module 216 can compare nutritional information from customer profile 213 to the cumulative nutritional content of food items 234A-234N. Based on the comparison, food item recommendation module 216 can determine that food items 234A-234N fail to satisfy a nutritional requirement of customer 222.

Method 300 identifying an additional food item that satisfies the nutritional requirement based on the customer nutritional profile and the nutritional content of the additional food item (305). For example, food item recommendation module 216 can identify food item 237 to satisfy the nutritional requirement based on information in customer profile 213 and information for food item 237 contained in product information 214.

Method 300 recommending the additional food item to the registered customer for purchase (306). For example, food item recommendation module 216 can send food item recommendation 232 to portable electronic device 201. Food item recommendation 232 recommends that customer 222 purchase item 237.

Figure 4:
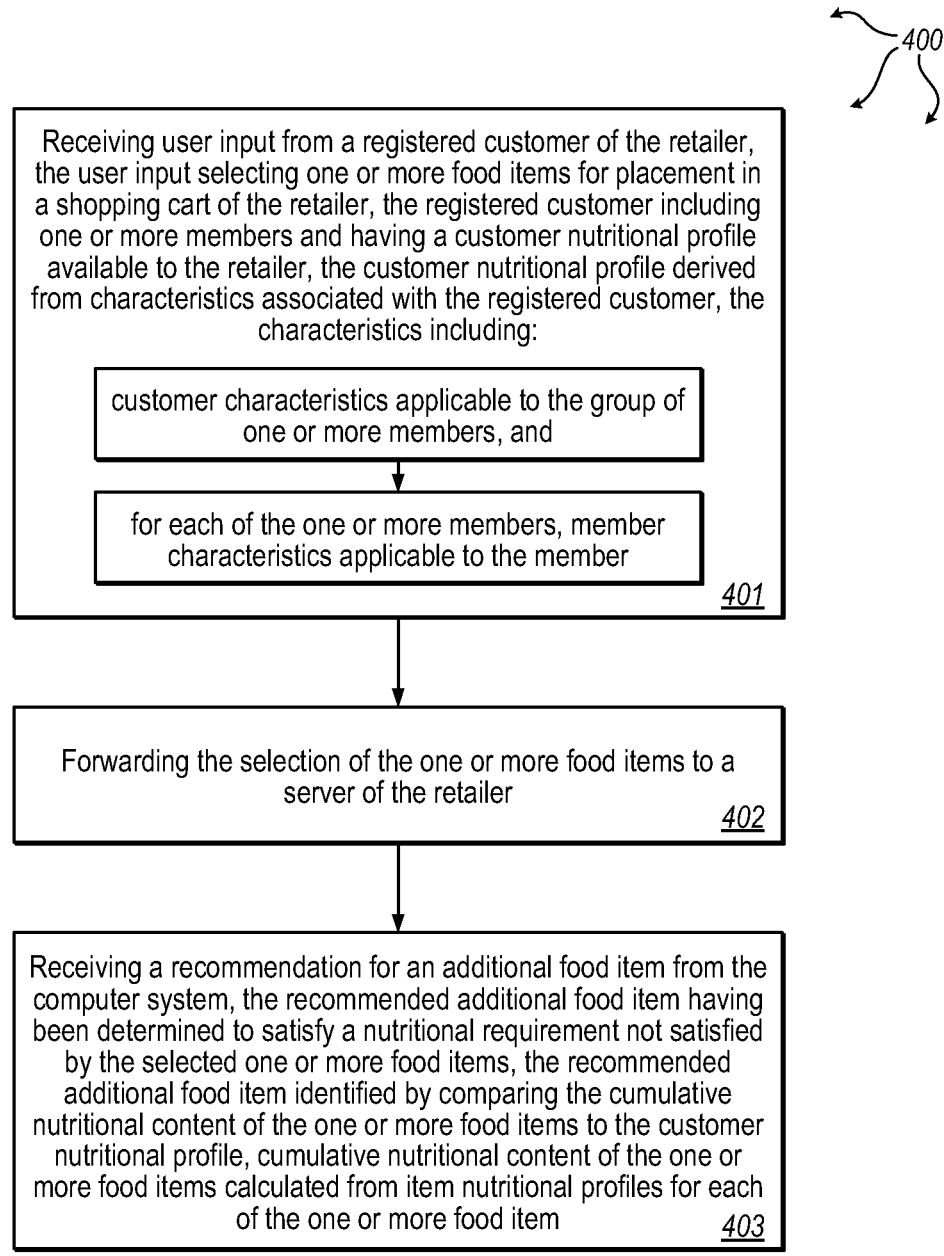
FIG. 4 illustrates a flow chart of an example method for recommending food items.

FIG. 4 illustrates a flow chart of an example method 400 for recommending food items. Method 400 will be described with respect to the components and date in computer architecture 200.

Method 400 includes receiving user input from a registered customer of the merchant, the user input selecting one or more food items for placement in a shopping cart of the merchant, the registered customer including one or more members and having a customer nutritional profile available to the merchant, the customer nutritional profile derived from characteristics associated with the registered customer, the characteristics including customer characteristics applicable to the group of one or more members, and for each of the one or more members, member characteristics applicable to the member (401). For example, customer 222 can enter input 233 to select food items 234A-234N for placement in a merchant shopping cart. As described, nutritional information and requirement for customer 222 can be contained in customer profile 213.

Method 400 includes forwarding the selection of the one or more food items to a server of the merchant (402). For example, merchant module 226 can forward food item indication 231, indicating selection of food items 234A-234N for purchase, to merchant computer system 211.

Method 400 includes receiving a recommendation for an additional food item from the server, the recommended additional food item having been determined to satisfy a nutritional requirement not satisfied by the selected one or more food items, the recommended additional food item identified by comparing the cumulative nutritional content of the one or more food items to the customer nutritional profile, cumulative nutritional content of the one or more food items calculated from item nutritional profiles for each of the one or more food items (403). For example, merchant module 226 can receive item recommendation 232, to purchase food item 237, from merchant computer system 211. As described, food item 237 can be identified as satisfying a national requirement not otherwise satisfied by food items 234A-234N.

As customer 222 places food item 237 and/or other food items in the shopping cart, merchant module 226 can send updates to merchant computer system 211. In response to the updates, food item recommendation module 216 compares an updated combined nutritional content of food items in the shopping cart with nutritional requirements in customer nutritional profile 213. Food item recommendation module 216 can send another recommendation to portable electronic device 201 based on the updated comparison. The update process can continue until a customer nutritional requirement is met or the customer checks out.

Thus, aspects of the invention can include an intelligent food recommendation system based on shopping cart contents as well as scientific nutritional data for an item, family demographics, consumption pattern, medical history, and takes into account current item prices and discounts being offered by a merchant (or manufacturer).

Aspects of the invention are applicable to both online customers and in-store customers. An in-store customer can be mapped to a corresponding registered (i.e., online) customer. In-store data and online data can be tracked collectively or separately. The availability of both in-store and online data for a customer enables a merchant computer system to improve food item recommendations for the customer.

In one aspect an in-store customer's mobile device can transmit an identifier. The identifier can be mapped to the corresponding registered customer. During in-store checkout, a Point-Of-Sale (POS) terminal can match purchased items to the registered customer using the identifier. Food items purchased in-store can be considered when making food item recommendations during subsequent online purchases.

Alternatively or in combination, the customer might scan items with a mobile device while shopping in a physical store location. An indication of scanned items can be sent from the mobile device (e.g., via merchant module 226) to merchant computer system 211. Merchant computer system 211 can then provide food item recommendations back to the mobile device while the customer is in the physical store location.

The foregoing description has been presented for the purposes of illustration and description. It is not intended to be exhaustive or to limit the invention to the precise form disclosed. Many modifications and variations are possible in light of the above teaching. Further, it should be noted that any or all of the aforementioned alternate embodiments may be used in any combination desired to form additional hybrid embodiments of the invention.

Further, although specific embodiments of the invention have been described and illustrated, the invention is not to be limited to the specific forms or arrangements of parts so described and illustrated. The scope of the invention is to be defined by the claims appended hereto, any future claims submitted here and in different applications, and their equivalents.

What is claimed:

1. At a computer system, a method for recommending a food item to a registered customer comprising a group of one or more members, the method comprising:
   accessing an indication of two or more food items in a shopping cart for the registered customer;
   accessing a customer nutritional profile for the registered customer, the customer nutritional profile derived from characteristics associated with the registered customer, the characteristics comprising:
      customer characteristics applicable to the group of one or more members; and
      for each member of the group of one or more members, member characteristics applicable to each member of the group of one or more members;
   calculating a cumulative nutritional content of the two or more food items from item nutritional profiles for each of the two or more food items;
   comparing the customer nutritional profile to the cumulative nutritional content to determine that purchase of the two or more food items fails to satisfy at least one nutritional requirement of the registered customer;
   identifying an additional food item that satisfies the at least one nutritional requirement based at least in part on the customer nutritional profile and a nutritional content of the additional food item; and
   recommending the additional food item to the registered customer for purchase in addition to the purchase of the two or more food items.

2. The method of claim 1, wherein the member characteristics comprise birthdate and gender.

3. The method of claim 1, wherein the member characteristics applicable to each member of the group of one or more members comprise a member nutritional profile for each member of the group of one or more members based at least in part on medical information for each member of the group of one or more members.

4. The method of claim 3, wherein the customer nutritional profile is based at least in part on the member nutritional profile for each member of the group of one or more members.

5. The method of claim 3, wherein:
   the medical information for each member of the group of one or more members comprises one or more diseases of each member of the group of one or more members.

6. The method of claim 1, wherein the identifying is further based at least in part on a price of each of the two or more food items.

7. The method of claim 6, further comprising updating the price of each of the two or more food items.

8. The method of claim 1, wherein:
   the member characteristics comprise birthdate and gender;
   the member characteristics applicable to each member of the group of one or more members comprise a member nutritional profile for each member of the group of one or more members based at least in part on medical information for each member of the group of one or more members;
   the medical information for each member of the group of one or more members comprises one or more diseases of each member of the group of one or more members;
   the customer nutritional profile is based at least in part on the member nutritional profile for each member of the group of one or more members;
   the identifying is further based at least in part on a price of each of the two or more food items; and
   the method further comprising:
      updating the price of each of the two or more food items.

9. At a portable electronic device, a method for receiving a food item recommendation from a merchant, the method comprising:
   receiving user input from a registered customer of the merchant, the user input selecting two or more food items for placement in a shopping cart of the merchant, the registered customer comprising one or more members and having a customer nutritional profile available to the merchant, the customer nutritional profile derived from characteristics associated with the registered customer, the characteristics comprising:
      customer characteristics applicable to the one or more members; and
      for each of the one or more members, member characteristics applicable to each member of the one or more members;
   forwarding the selection of the two or more food items to a computer server of the merchant; and
   receiving a recommendation for an additional food item from the computer server in addition to the two or more food items, the additional food item recommended having been determined to satisfy at least one nutritional requirement not satisfied by the selection of the two or more food items, the additional food item recommended identified by comparing a cumulative nutritional content of the two or more food items to the customer nutritional profile, the cumulative nutritional content of the two or more food items calculated from an item nutritional profile for each of the two or more food items.

10. The method of claim 9, wherein the member characteristics comprise age and gender.

11. The method of claim 9, wherein the member characteristics comprise medical information.

12. The method of claim 11, wherein:
the medical information comprises one or more diseases.

13. The method of claim 9, wherein the customer nutritional profile is based at least in part on member nutritional profiles of the one or more members.

14. The method of claim 9, wherein the portable electronic device detects an identifier for each food item of the two or more food items in the shopping cart and sends the identifier to the merchant.

15. The method of claim 9, wherein:
the member characteristics comprise age and gender;
the member characteristics comprise medical information;
the medical information comprises one or more diseases;
the customer nutritional profile is based at least in part on member nutritional profiles of the one or more members;
the portable electronic device detects an identifier for each food item in the shopping cart and sends the identifier to the merchant; and
the portable electronic device detects an identifier for each food item of the two or more food items in the shopping cart and sends the identifier to the merchant.

16. At a merchant computer system, the merchant computer system comprising:
one or more processors;
non-transitory system memory; and
one or more computer storage devices having stored thereon computer-executable instructions representing a food item recommendation module, the food item recommendation module configured to:
access an indication of two or more food items in a shopping cart for a registered customer of a merchant, the registered customer comprising a group of one or more members;
access a customer nutritional profile for the registered customer, the customer nutritional profile derived from characteristics associated with the registered customer, the characteristics comprising:
customer characteristics applicable to the group of one or more members; and
for each member of the group of one or more members, member characteristics applicable to each member of the group of one or more members;
calculate a cumulative nutritional content of the two or more food items from item nutritional profiles for each of the two or more food items;
compare the customer nutritional profile to the cumulative nutritional content to determine that purchase of the two or more food items fails to satisfy at least one nutritional requirement of the registered customer;
identify an additional food item that satisfies the at least one nutritional requirement based at least in part on the customer nutritional profile and a nutritional content of the additional food item; and
recommend the additional food item to the registered customer for purchase in addition to the purchase of the two or more food items.

17. The merchant computer system of claim 16, wherein the member characteristics comprise birthdate and gender.

18. The merchant computer system of claim 16, wherein the member characteristics applicable to each member of the group of one or more members comprise a member nutritional profile for each member of the group of one or more members based at least in part on medical information for each member of the group of one or more members.

19. The merchant computer system of claim 18, wherein the customer nutritional profile is based at least in part on the member nutritional profile for each member of the group of one or more members.

20. The merchant computer system of claim 18, wherein:
the medical information for each member of the group of one or more members comprises one or more diseases of each member of the group of one or more members.

21. The merchant computer system of claim 16, wherein the identifying is further based at least in part on a price of each of the two or more food items.

22. The merchant computer system of claim 16, wherein:
the member characteristics comprise birthdate and gender;
the member characteristics applicable to each member of the group of one or more members comprise a member nutritional profile for each member of the group of one or more members based at least in part on medical information for each member of the group of one or more members;
the customer nutritional profile is based at least in part on the member nutritional profile for each member of the group of one or more members;
the medical information of the member comprises one or more diseases of each member of the group of one or more members; and
the identifying is further based at least in part on a price of each of the two or more food items.

* * * * *